(12) United States Patent
D'Ambrosio et al.

(10) Patent No.: US 8,620,447 B2
(45) Date of Patent: Dec. 31, 2013

(54) TRANSCUTANEOUS ENERGY TRANSFER COIL WITH INTEGRATED RADIO FREQUENCY ANTENNA

(75) Inventors: Ralph L. D'Ambrosio, Wenham, MA (US); Martin Kortyka, Eschweiler (DE)

(73) Assignee: Abiomed Inc., Danvers, MA (US)

( * ) Notice: Subject to any disclaimer, the term of this patent is extended or adjusted under 35 U.S.C. 154(b) by 0 days.

(21) Appl. No.: 13/328,636

(22) Filed: Dec. 16, 2011

(65) Prior Publication Data

US 2012/0265003 A1 Oct. 18, 2012

Related U.S. Application Data

(60) Provisional application No. 61/475,573, filed on Apr. 14, 2011.

(51) Int. Cl.
*A61N 1/00* (2006.01)

(52) U.S. Cl.
USPC .............................................. 607/61; 600/16

(58) Field of Classification Search
USPC .............................................. 607/61; 600/16
See application file for complete search history.

(56) References Cited

U.S. PATENT DOCUMENTS

| | | | |
|---|---|---|---|
| 3,195,038 A | 7/1965 | Fry | |
| 3,195,540 A | 7/1965 | Waller | |
| 3,357,432 A | 12/1967 | Sparks | |
| 3,357,434 A | 12/1967 | Abell | |
| 3,711,747 A | 1/1973 | Sahara et al. | |
| 3,756,246 A | 9/1973 | Thaler et al. | |
| 3,824,129 A | 7/1974 | Fagan, Jr. | |
| 3,825,925 A | 7/1974 | Drusch | |
| 3,866,616 A | 2/1975 | Purdy et al. | |
| 3,867,950 A | 2/1975 | Fischell | |
| 3,888,260 A | 6/1975 | Fischell | |
| 3,915,038 A | 10/1975 | Malin | |
| 3,934,177 A | 1/1976 | Horbach | |
| 3,942,535 A | 3/1976 | Schulman | |
| 3,987,799 A | 10/1976 | Purdy et al. | |
| 3,995,137 A | 11/1976 | Okada et al. | |
| 4,011,499 A | 3/1977 | Betsill et al. | |

(Continued)

FOREIGN PATENT DOCUMENTS

DE 2720011 A1 11/1978
EP 0 507 360 A2 10/1992

(Continued)

OTHER PUBLICATIONS

[No Author Listed] SBS 1.1-Compliant Gas Gauge and Protection Enabled with Impedance Track™, Texas Instruments, SLUS757B—Jul. 2007, Revised Apr. 2008. 18 pages. [No Author Listed] Low-power SoC (system-on-chip) with MCU, memory sub-1 ghz RF transceiver, and USB controller. TIRF Common Spec (CC1110Fx/CC1111Fx), Texas Instruments, Jul. 20, 2010, 247 pages.
[No Author Listed]Battery Spec NCR 18650. NNP Series. Panasonic. Feb. 2010, 1 page.

(Continued)

*Primary Examiner* — Christopher D Koharski
*Assistant Examiner* — Michael Carey
(74) *Attorney, Agent, or Firm* — Thomas J. Engellenner; Reza Mollaaghababa; Pepper Hamilton LLP (57) ABSTRACT

Improved methods and devices for communicating via radio frequency (RF) in transcutaneous energy transfer (TET) systems is provided. In particular, an improved implantable coil for use in a transcutaneous energy transfer (TET) system is provided having an integrated radio frequency (RF) antenna. Further, a method of communicating between an external device and an implanted device having a plurality of secondary coils with integrated RF antennas is also provided.

21 Claims, 7 Drawing Sheets

(56) References Cited

U.S. PATENT DOCUMENTS

| | | | |
|---|---|---|---|
| 4,012,769 A | 3/1977 | Edwards et al. |
| 4,041,955 A | 8/1977 | Kelly et al. |
| 4,068,292 A | 1/1978 | Berry et al. |
| 4,071,032 A | 1/1978 | Schulman |
| 4,104,701 A | 8/1978 | Baranowski |
| 4,134,408 A | 1/1979 | Brownlee et al. |
| 4,143,661 A | 3/1979 | LaForge et al. |
| 4,186,749 A | 2/1980 | Fryer |
| 4,266,533 A | 5/1981 | Ryaby et al. |
| 4,441,210 A | 4/1984 | Hochmair et al. |
| 4,441,498 A | 4/1984 | Nordling |
| 4,517,585 A | 5/1985 | Ridout et al. |
| 4,539,433 A | 9/1985 | Ishino et al. |
| 4,586,508 A | 5/1986 | Batina et al. |
| 4,665,896 A | 5/1987 | LaForge et al. |
| 4,673,888 A | 6/1987 | Engelmann et al. |
| 4,678,986 A | 7/1987 | Barthelemy |
| 4,679,560 A | 7/1987 | Galbraith |
| 4,716,353 A | 12/1987 | Engelmann |
| 4,717,889 A | 1/1988 | Engelmann |
| 4,741,339 A | 5/1988 | Harrison et al. |
| 4,808,924 A | 2/1989 | Cecco et al. |
| 4,837,497 A | 6/1989 | Leibovich |
| 4,924,171 A | 5/1990 | Baba et al. |
| 4,925,443 A | 5/1990 | Heilman et al. |
| 4,944,299 A | 7/1990 | Silvian |
| 5,000,178 A | 3/1991 | Griffith |
| 5,004,489 A | 4/1991 | Rotman |
| 5,109,843 A | 5/1992 | Melvin et al. |
| 5,214,392 A | 5/1993 | Kobayashi et al. |
| 5,312,439 A | 5/1994 | Loeb |
| 5,314,453 A | 5/1994 | Jeutter |
| 5,324,316 A | 6/1994 | Schulman et al. |
| 5,350,411 A | 9/1994 | Ryan et al. |
| 5,350,413 A | 9/1994 | Miller et al. |
| 5,355,296 A | 10/1994 | Kuo et al. |
| 5,358,514 A | 10/1994 | Schulman et al. |
| 5,383,912 A | 1/1995 | Cox et al. |
| 5,411,536 A | 5/1995 | Armstrong |
| 5,411,537 A | 5/1995 | Munshi et al. |
| 5,480,415 A | 1/1996 | Cox et al. |
| 5,506,503 A | 4/1996 | Cecco et al. |
| 5,527,348 A | 6/1996 | Winkler et al. |
| 5,545,191 A | 8/1996 | Mann et al. |
| 5,556,421 A | 9/1996 | Prutchi et al. |
| 5,569,156 A | 10/1996 | Mussivand |
| 5,613,935 A | 3/1997 | Jarvik |
| 5,621,369 A | 4/1997 | Gardner et al. |
| 5,630,836 A | 5/1997 | Prem et al. |
| 5,690,693 A | 11/1997 | Wang et al. |
| 5,702,431 A | 12/1997 | Wang et al. |
| 5,713,939 A | 2/1998 | Nedungadi et al. |
| 5,722,998 A | 3/1998 | Prutchi et al. |
| 5,730,125 A | 3/1998 | Prutchi et al. |
| 5,733,313 A | 3/1998 | Barreras, Sr. et al. |
| 5,735,887 A | 4/1998 | Barreras, Sr. et al. |
| 5,740,257 A | 4/1998 | Marcus |
| 5,741,316 A | 4/1998 | Chen et al. |
| 5,749,909 A | 5/1998 | Schroeppel et al. |
| 5,755,748 A | 5/1998 | Borza et al. |
| 5,861,019 A * | 1/1999 | Sun et al. ................ 607/60 |
| 5,948,006 A | 9/1999 | Mann |
| 5,951,459 A | 9/1999 | Blackwell |
| 5,959,522 A | 9/1999 | Andrews |
| 5,963,132 A | 10/1999 | Yoakum |
| 5,978,713 A | 11/1999 | Prutchi et al. |
| 5,991,665 A | 11/1999 | Wang et al. |
| 5,995,874 A | 11/1999 | Borza et al. |
| 6,047,214 A | 4/2000 | Mueller et al. |
| 6,048,601 A | 4/2000 | Yahagi et al. |
| 6,058,330 A | 5/2000 | Borza et al. |
| 6,067,474 A | 5/2000 | Schulman et al. |
| 6,141,592 A | 10/2000 | Pauly |
| 6,144,841 A | 11/2000 | Feeney |
| 6,149,683 A | 11/2000 | Lancisi et al. |
| 6,212,430 B1 | 4/2001 | Kung |
| 6,243,608 B1 | 6/2001 | Pauly et al. |
| 6,275,737 B1 | 8/2001 | Mann |
| 6,278,258 B1 | 8/2001 | Echarri et al. |
| 6,321,118 B1 | 11/2001 | Hahn |
| 6,324,430 B1 | 11/2001 | Zarinetchi et al. |
| 6,324,431 B1 | 11/2001 | Zarinetchi et al. |
| 6,327,504 B1 | 12/2001 | Dolgin et al. |
| 6,349,234 B2 | 2/2002 | Pauly et al. |
| 6,366,817 B1 | 4/2002 | Kung |
| 6,389,318 B1 | 5/2002 | Zarinetchi et al. |
| 6,395,027 B1 | 5/2002 | Snyder |
| 6,400,991 B1 | 6/2002 | Kung |
| 6,415,186 B1 | 7/2002 | Chim et al. |
| 6,430,444 B1 | 8/2002 | Borza et al. |
| 6,442,434 B1 | 8/2002 | Zarinetchi et al. |
| 6,443,891 B1 | 9/2002 | Grevious |
| 6,445,956 B1 | 9/2002 | Laird et al. |
| 6,478,820 B1 | 11/2002 | Weiss |
| 6,496,733 B2 | 12/2002 | Zarinetchi et al. |
| 6,507,759 B1 | 1/2003 | Prutchi et al. |
| 6,542,777 B1 | 4/2003 | Griffith et al. |
| 6,553,263 B1 | 4/2003 | Meadows et al. |
| 6,591,139 B2 | 7/2003 | Loftin et al. |
| 6,631,296 B1 | 10/2003 | Parramon et al. |
| 6,745,077 B1 | 6/2004 | Griffith et al. |
| 6,772,011 B2 | 8/2004 | Dolgin |
| 6,959,213 B2 | 10/2005 | Prutchi et al. |
| 6,959,217 B2 | 10/2005 | DelMain et al. |
| 6,968,234 B2 * | 11/2005 | Stokes ............................. 607/36 |
| 7,015,769 B2 | 3/2006 | Schulman et al. |
| 7,062,331 B2 | 6/2006 | Zarinetchi et al. |
| 7,076,304 B2 | 7/2006 | Thompson |
| 7,079,901 B1 | 7/2006 | Loftin et al. |
| 7,092,762 B1 | 8/2006 | Loftin et al. |
| 7,151,914 B2 | 12/2006 | Brewer |
| 7,155,291 B2 | 12/2006 | Zarinetchi et al. |
| 7,177,690 B2 | 2/2007 | Woods et al. |
| 7,184,836 B1 | 2/2007 | Meadows et al. |
| 7,191,007 B2 | 3/2007 | Desai et al. |
| 7,225,032 B2 | 5/2007 | Schmeling et al. |
| 7,237,712 B2 | 7/2007 | DeRocco et al. |
| 7,248,929 B2 | 7/2007 | Meadows et al. |
| 7,286,880 B2 | 10/2007 | Olson et al. |
| 7,286,881 B2 | 10/2007 | Schommer et al. |
| 7,295,878 B1 | 11/2007 | Meadows et al. |
| 7,308,316 B2 | 12/2007 | Schommer |
| 7,418,297 B2 | 8/2008 | Bornhoft et al. |
| 7,437,644 B2 | 10/2008 | Ginggen et al. |
| 7,471,986 B2 | 12/2008 | Hatlestad |
| 7,482,783 B2 | 1/2009 | Schommer |
| 7,512,443 B2 | 3/2009 | Phillips et al. |
| 7,515,012 B2 | 4/2009 | Schulman et al. |
| 7,515,967 B2 | 4/2009 | Phillips et al. |
| 7,532,932 B2 | 5/2009 | Denker et al. |
| 7,599,743 B2 | 10/2009 | Hassler, Jr. et al. |
| 7,599,744 B2 * | 10/2009 | Giordano et al. ............... 607/61 |
| 7,632,235 B2 | 12/2009 | Karicherla |
| 7,658,196 B2 | 2/2010 | Ferreri et al. |
| 7,689,176 B2 | 3/2010 | Crivelli |
| 7,711,435 B2 | 5/2010 | Schommer |
| 7,738,965 B2 | 6/2010 | Phillips et al. |
| 7,751,899 B1 | 7/2010 | Karunasiri |
| 7,751,902 B1 | 7/2010 | Karunasiri |
| 7,775,444 B2 | 8/2010 | DeRocco et al. |
| 7,813,801 B2 | 10/2010 | Youker et al. |
| 7,818,068 B2 | 10/2010 | Meadows et al. |
| 7,822,480 B2 | 10/2010 | Park et al. |
| 7,848,814 B2 | 12/2010 | Torgerson et al. |
| 7,856,986 B2 | 12/2010 | Darley |
| 2002/0016568 A1 | 2/2002 | Lebel et al. |
| 2003/0088295 A1 * | 5/2003 | Cox ............................ 607/60 |
| 2003/0163020 A1 | 8/2003 | Frazier |
| 2003/0171792 A1 | 9/2003 | Zarinetchi et al. |
| 2005/0075693 A1 | 4/2005 | Toy et al. |
| 2005/0075696 A1 | 4/2005 | Forsberg et al. |
| 2005/0107847 A1 | 5/2005 | Gruber et al. |
| 2005/0113887 A1 | 5/2005 | Bauhahn et al. |
| 2005/0288739 A1 | 12/2005 | Hassler et al. |

(56) References Cited

U.S. PATENT DOCUMENTS

| | | | |
|---|---|---|---|
| 2005/0288740 | A1 | 12/2005 | Hassler et al. |
| 2005/0288743 | A1 | 12/2005 | Ahn et al. |
| 2006/0020300 | A1 | 1/2006 | Nghiem et al. |
| 2006/0020305 | A1 | 1/2006 | Desai et al. |
| 2006/0107148 | A1 | 5/2006 | Ginggen et al. |
| 2006/0197494 | A1 | 9/2006 | Schommer |
| 2006/0247737 | A1 | 11/2006 | Olson et al. |
| 2007/0049983 | A1* | 3/2007 | Freeberg .................. 607/32 |
| 2007/0106274 | A1 | 5/2007 | Ayre et al. |
| 2007/0142696 | A1 | 6/2007 | Crosby et al. |
| 2007/0255349 | A1 | 11/2007 | Torgerson et al. |
| 2007/0270921 | A1* | 11/2007 | Strother et al. .............. 607/60 |
| 2008/0027500 | A1 | 1/2008 | Chen |
| 2008/0027513 | A1* | 1/2008 | Carbunaru .................. 607/60 |
| 2008/0065290 | A1 | 3/2008 | Breed |
| 2008/0129517 | A1 | 6/2008 | Crosby et al. |
| 2008/0167531 | A1 | 7/2008 | McDermott |
| 2008/0312852 | A1 | 12/2008 | Maack |
| 2009/0069869 | A1 | 3/2009 | Stouffer et al. |
| 2009/0157148 | A1 | 6/2009 | Phillips et al. |
| 2009/0273349 | A1 | 11/2009 | Rondoni et al. |
| 2009/0276016 | A1 | 11/2009 | Phillips et al. |
| 2010/0063347 | A1 | 3/2010 | Yomtov |
| 2010/0076524 | A1 | 3/2010 | Forsberg et al. |
| 2010/0080025 | A1 | 4/2010 | Terlizzi |
| 2010/0222848 | A1 | 9/2010 | Forsell |
| 2010/0305662 | A1 | 12/2010 | Ozawa et al. |
| 2010/0312188 | A1 | 12/2010 | Robertson |
| 2011/0009924 | A1 | 1/2011 | Meskens |
| 2011/0101790 | A1 | 5/2011 | Budgett |
| 2011/0160516 | A1 | 6/2011 | Dague et al. |
| 2012/0154143 | A1 | 6/2012 | D'Ambrosio |
| 2012/0157753 | A1 | 6/2012 | D'Ambrosio |
| 2012/0157754 | A1 | 6/2012 | D'Ambrosio |
| 2012/0157755 | A1 | 6/2012 | D'Ambrosio |
| 2013/0158631 | A1 | 6/2013 | Shea et al. |

FOREIGN PATENT DOCUMENTS

| | | |
|---|---|---|
| JP | 07-046164 A | 2/1995 |
| JP | 2010-284065 A | 12/2010 |
| WO | 97/29802 A2 | 8/1997 |
| WO | 97/47065 A1 | 12/1997 |
| WO | 99/44684 A1 | 9/1999 |
| WO | 2006096685 A1 | 9/2006 |
| WO | 2008/106717 A1 | 9/2008 |
| WO | 2011008163 A1 | 1/2011 |

OTHER PUBLICATIONS

Abe et al., Development of transcutaneous energy transmission system for totally implantable artificial heart. Artificial Heart 2/Proceedings of the 2nd International Symposium on Artificial Heart and Assist Device. Akutsu, T. ed, Springer-Verlag, Tokyo, pp. 257-261, 1988.

Ahn et al., In Vivo Performance Evaluation of a Transcutaneous Energy and Information Transmission System for the Total Artificial Heart, ASAIO Journal 1993, M208-M212.

Barsukov, Theory and Implementation of Impedance Track™ Battery Fuel-Gauging Algorithm in bq20z8x Product Family, Texas Instruments, SLUA364, Nov. 2005. 8 pages.

Bearnson et al., Electronics Development for the Utah Electrohydrolic Total Artificial Heart. Sixth Annual IEEE Symposium on Computer-Based Medical Systems, 247-252 (1993).

Callewaert et al., A Programmable Implantable Stimulator with Percutaneous Optical Control. Ninth Annual Conference of the Engineering in Medicine and Biology Society IEEE, 1370-1371 (1987).

Davies et al., Adaptation of Tissue to a Chronic Heat Load, ASAIO Journal. 40(3), M514-7 (1994).

Donaldson, Nde N, Use of feedback with voltage regulators for implants powered by coupled coils. Med Biol Eng Comput. May 1985;23(3):291, XP002066875, ISSN: 0140-0118.

Fraim et al. Performance of a tuned ferrite core transcutaneous transformer. IEEE Trans Bio-med Eng. Sep. 1971; BME-18(5):352-9.

Galbraith et al, A Wide-Band Efficient Inductive Transdermal Power and Data Link with Coupling Insensitive Gain. IEEE Transactions on Biomedical Engineering, BME 34(4):265-275 (1987).

Geselowitz et al., The effects of metals on a transcutaneous energy transmission system. IEEE Transactions on Biomedical Engineering. vol. 39(9), pp. 928-934, Sep. 1992.

Masuzawa, T., et al., Set-up, Improvement, and Evaluation of an Electrohydraulic Total Artificial Heart with a Separately Placed Energy Converter. (1996) ASAIO Journal, vol. 42; M328-M332.

Matsuki et al. Energy Transferring System Reducing Temperature Rise for Implantable Power Consuming Devices. Proceedings of the 18th Annual Conference of the IEEE Engineering in Medicine and Biology Society, Amsterdam Oct. 31-Nov. 3, 1996, vol. 1, pp. 185-186.

Matsuki et al., Signal Transmission for Implantable Medical Devices using Figure-of-eight Coils, IEEE Transactions on Magnetics, vol. 32 No. 5, pp. 5121-5123, Sep. 1996.

Melvin, D.B., et al., Electric Power Induction Through an Isolated Intestinal Pouch. (1991) Trans. Am. Soc. Intern. Organs, vol. XXXVII;M203-M204.

Miller et al. Development of an Autotuned Transcutaneous Energy Transfer System. ASAIO Journal. 1993;39:M706-M710.

Mitamura et al. Development of an Implantable Motor-Driven Assist Pump System. IEEE Transactions on Biomedical Engineering. vol. 37(2), pp. 146-156, 1990.

Mitamura et al. A Transcutaneous Optical Information Transmission System for Implantable Motor-drive Artificial Hearts. ASAIO Transactions.1990;36:M278-M280.

Mohammed et al. A miniature DC-DC converter for energy producing implantable devices. IEEE Ninth Annual Conference of the Engineering in Medicine and Biology Society, 1147-1148, 1987.

Mohammed, Design of radio frequency powered coils for implantable stimulators. IEEE Ninth Annual Conference of the Engineering in Medicine and Biology Society, 1378-1379, 1987.

Mussivand et al. Remote energy transmission for powering artificial hearts and assist devices. Artificial Heart 6/6th International Symposium on Artificial Heart and Assist Devices. Akutsu et al., eds., Springer-Verlag, Tokyo, pp. 344-347, 1998.

Mussivand et al. Transcutaneous energy transfer system performance evaluation. Artificial Organs. May 1993;17 (11):940-947.

Myers et al. A transcutaneous power transformer. Transactions of the American Society for Artificial Internal Organs, vol. 14, pp. 210-214, 1968.

Phillips, R.P., A High Capacity Transcutaneous Energy Transmission System. ASAIO Journal, vol. 41: M259-M262 (1995).

Rintoul et al, Continuing Development of the Cleveland Clinic-Nimbus Total Artificial Heart. ASAIO Journal, 39: M168-171 (1993).

Rosenberg et al., Progress Towards a Totally Implantable Artificial Heart. Cardiovascular Science & Technology: Basic & Applied, I. Precised Proceedings, pp. 214-216 (1989-1990).

Sherman et al., Energy Transmission Across Intact Skin for Powering Artificial Internal Organs. Trans. Am. Soc. Artificial Intern Organs, vol. XXVII, 1981, pp. 137-141.

Sherman et al., Transcutaneous energy transmission (TET) system for energy intensive prosthetic devices. Progress in Artificial Organs. 1985;400-404.

Sutton, A miniaturized device for electrical energy transmission through intact skin-concepts and sesults of initial tests. Third Meeting of the International Society for Artificial Organs. vol. 5, abstracts, Jul. 1981, pp. 437-440.

Weiss et al. A telemetry system for the implanted total artificial heart and ventricular assist device. IEEE Ninth Annual Conference of the Engineering in medicine and Biology Society, pp. 186-187, 1987.

Weiss et al., Permanent Circulatory Support at the Pennsylvania State University. IEEE Transaction on Biomedical Engineering 37(2):138-145 (Feb. 1990).

International Search Report and Written Opinion for Application No. PCT/US2011/065477, mailed Nov. 28, 2012. (10 pages).

* cited by examiner

TRANSCUTANEOUS ENERGY TRANSFER COIL WITH INTEGRATED RADIO FREQUENCY ANTENNA

RELATED APPLICATIONS

This application claims priority to U.S. Provisional Application Ser. No. 61/475,573, filed on Apr. 14, 2011, and entitled "Transcutaneous Energy Transfer Coil with Integrated Radio Frequency Antenna."

FIELD

The present invention relates to transcutaneous energy transfer (TET) systems and, in particular, to TET systems having an integrated radio frequency (RF) antenna.

BACKGROUND

In a variety of scientific, industrial, and medically related applications, it can be desirable to transfer energy or power across some type of boundary. For example, one or more devices that require power can be located within the confines of a fully sealed or contained system in which it can be difficult and/or undesirable to include a substantial and/or long term source of power. It can also be undesirable to repeatedly enter the closed system for a variety of reasons. In these cases, a power source external to the fully sealed or contained system and some feasible means of transferring power from the external source to one or more internal devices without direct electrical conduction can be preferable.

One example of a closed system is the human body. In several medically related and scientific applications, a variety of prosthetic and other devices that require power can be surgically implanted within various portions of the body. Examples of such devices include a synthetic replacement heart, a circulatory blood pump or ventricular assist device (VAD), a cochlear implant, a pacemaker, and the like. With respect to the human body, complications associated with repeated surgical entry make replaceable internal power sources impractical. Likewise, the risk of infection and/or dislodgment make direct electrical linkages between external power supplies and implanted devices undesirable.

Accordingly, transcutaneous energy transfer (TET) systems are employed to transfer energy from outside the body to inside the body in order to provide power to one or more implanted devices from an external power source. TET systems use an inductive link to transfer power without puncturing the skin. Thus, the possibility of infection is reduced while comfort and convenience for patients is increased.

TET devices typically include an external primary coil and an implanted secondary coil that are separated by intervening layers of tissue. The primary coil is designed to induce alternating current in the subcutaneously placed secondary coil, typically for transformation to direct current to power an implanted device. TET devices therefore also typically include electrical circuits for periodically providing appropriate alternating current to the primary coil. These circuits typically receive their power from an external power source.

As implanted medical devices have become increasingly complex, a need has developed to also provide data communication between the implanted devices and an outside operator, such as a physician or scientist. As with the transfer of power, it can be desirable to provide a method of communication that does not require a physical connection, e.g., wires passing through the skin, between the implanted device and external monitors or controllers.

Radio frequency (RF) communication systems have been developed to address the need for bi-directional data communication between operators and/or patients and implanted medical devices. These systems are components of the implanted system and use a separate RF antenna so that an external controller or programmer can communicate with internal sensors or control elements. Typically, the separate RF antenna is implanted in a patient away from the implanted secondary TET coil to avoid radio interference when the coil is in use.

Prior art RF antennas have several disadvantages. First, they suffer from signal attenuation. RF antennas are often implanted deeper within a patient's body than the secondary TET coil, for example, within the chest or in the abdominal cavity. Placing the RF antenna in such a location requires communicating through a large amount of muscle, skin, and fat, resulting in a large amount of signal attenuation during use.

Second, the use of a separate RF communication antenna means there is yet another component that must be implanted into a patient's body and connected to an implanted device controller or other implanted circuitry. Having this additional component increases the complexity of the system, requires a more invasive surgery to implant, and provides another possible point of failure in the system.

Thus, a need exists for a better performing and more integrated RF antenna for use in a TET system.

SUMMARY

To overcome the above and other drawbacks of conventional systems, the present invention provides an improved secondary coil for use in a transcutaneous energy transfer (TET) system having an integrated radio frequency (RF) antenna and methods for use.

One aspect of the invention provides an implantable coil for use in a TET system including a coil winding, circuitry in electrical communication with the coil winding, and a RF antenna. The coil winding is adapted to produce an electric current in the presence of a time-varying magnetic field operating at a first frequency. The circuitry can be adapted to receive and condition the electric current produced in the coil winding. The RF antenna can be configured to operate at a second frequency different from the first frequency.

In one embodiment of the invention, the power conditioning circuitry can be contained within a ferrite core in the implantable coil. The ferrite core can isolate the circuitry from both the TET and RF antenna operating frequencies.

The coil winding, ferrite core, circuitry, and RF antenna can further be encapsulated in a biocompatible material. In certain embodiments, the encapsulating biocompatible material can be epoxy. In other embodiments, the biocompatible material can be a polyurethane, such as ANGIOFLEX®, a polyether-based polyurethane plastic manufactured by Abiomed, Inc. of Danvers, Mass. In still other embodiments, the biocompatible material can be a silicone rubber compound.

In one embodiment, the coil winding can be operated at a frequency below about 30 MHz, which is an operating range that minimizes tissue-related attenuation. In other embodiments, the coil winding can be operated at a first frequency of about 300 KHz. In still other embodiments, the coil winding can be operated at a first frequency of 327 KHz. The term "about" as used herein typically refers to a range of +/−10%, more preferably +/−5% or +/−3%.

The RF antenna can be operated at any frequency suitable for RF communication. In some embodiments, the RF antenna can be operated at a second frequency of about 900 MHz. In other embodiments, the RF antenna can be operated at a second frequency in the range of about 902 MHz to about 928 MHz. In still other embodiments, the RF antenna can be operated at a second frequency in the range of about 863 MHz to about 870 MHz.

In one embodiment of the invention, the RF antenna can be a micro-strip patch antenna. In other embodiments, the RF antenna can be a micro-strip patch antenna laminated to the ferrite core of the implantable coil.

In still other embodiments of the invention, the RF antenna can be a loop antenna. In certain other embodiments, the coil winding can be used as the RF antenna, which reduces complexity and improves reliability of the implantable system.

In one embodiment of the invention, the implantable coil further includes a connecting portion containing one or more wires connected to the coil winding and the RF antenna in order to facilitate connecting the coil to an implanted controller.

In a second aspect of the invention, a transcutaneous energy transfer system is provided including a secondary coil adapted for disposition in a patient, an external primary coil configured to transmit transcutaneous energy to the secondary coil, and a controller. The secondary coil includes a coil winding adapted to receive transcutaneous energy and a RF antenna. The controller, which is also adapted for disposition in a patient, includes circuitry to direct electric current from the secondary coil to charge a storage device and/or power an implantable assist device.

In one embodiment of the invention, the controller can be configured to communicate with an external communicator using the RF antenna in the secondary coil. The external communicator can be part of the external TET driver or a separate unit.

In other embodiments, the TET system can be provided with more than one secondary coil adapted for disposition in a patient. Each coil can include a coil winding and a RF antenna. Having more than one implanted secondary coil provides advantages of redundancy and signal path selection. In some embodiments, the controller can be configured to scan among the secondary coils for a RF antenna having the highest RF signal quality and select the RF antenna having the highest signal quality for use in communicating with an external device. In still other embodiments, the controller can be further configured to resume scanning among the plurality of secondary coils after completing communication with the external device.

In another aspect of the invention, a method of communicating between an external device and an implanted device in a transcutaneous energy transfer (TET) system is provided. The method includes the steps of scanning among a plurality of implanted secondary coils having integrated radio frequency (RF) antennas to determine which RF antenna has the best RF signal quality. The method further includes selecting the RF antenna having the best RF signal quality for a communication exchange between the external device and the implanted device. The method also includes resuming scanning among the plurality of implanted secondary coils to determine whether an other RF antenna exhibits a better RF signal quality.

In some embodiments, the method can further include switching to the other RF antenna that exhibits better RF signal quality for a communication exchange.

BRIEF DESCRIPTION OF THE DRAWINGS

The invention will be more fully understood from the following detailed description taken in conjunction with the accompanying drawings, in which.

DETAILED DESCRIPTION

Certain exemplary embodiments will now be described to provide an overall understanding of the principles of the methods and devices disclosed herein. One or more examples of these embodiments are illustrated in the accompanying drawings. Those skilled in the art will understand that the methods and devices specifically described herein and illustrated in the accompanying drawings are non-limiting exemplary embodiments and that the scope of the present invention is defined solely by the claims. The features illustrated or described in connection with one exemplary embodiment can be combined with the features of other embodiments. Such modifications and variations are intended to be included within the scope of the present invention.

A transcutaneous energy transfer (TET) system works by inductively coupling an external primary coil winding to an implanted secondary coil winding. The primary coil can be connected to a power source and creates a time-varying magnetic field. When properly aligned with a secondary coil, the time-varying magnetic field from the primary coil induces an alternating electric current in the secondary coil. The secondary coil can be connected to a controller that harnesses the electric current and uses it to, for example, charge a battery pack or power an implantable device like a ventricular assist device (VAD), or other implantable assist device. By utilizing induction to transfer energy, TET systems avoid having to maintain an open passage through a patient's skin to power an implantable device.

Figure 1:
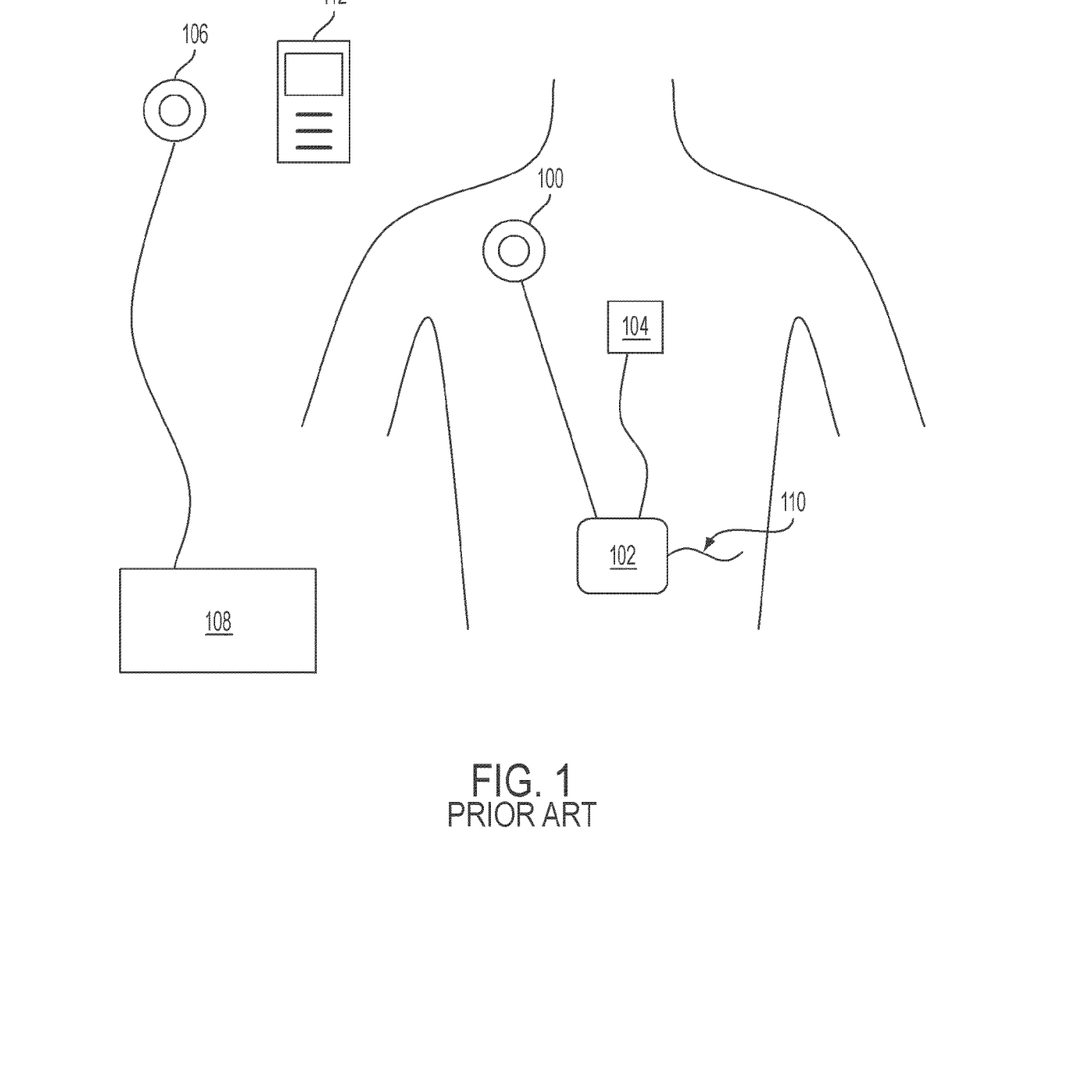
FIG. 1 is an illustration of a transcutaneous energy transfer (TET) system of the prior art.

FIG. 1 illustrates a modern TET system known in the prior art. The system includes an external primary coil 106 that is connected to a power supply 108, as well as a separate external RF communicator 112. Implanted inside a patient is a secondary coil 100 adapted to receive energy from primary coil 106, a controller 102, a VAD 104 or other implanted assist device, and a radio frequency (RF) antenna 110.

In use, primary coil 106 can be placed over the area of secondary coil 100 such that they are substantially in axial alignment. In this position, the primary coil 106 does not impede the RF transmission between the external communicator 112 and the secondary coil 100. The secondary coil 100 can be implanted at various locations in the body, but is often implanted close to the skin to minimize the number of layers of tissue disposed between primary coil 106 and secondary coil 100. Power source 108, which can include conditioning circuitry to produce a desired output voltage and current profile, can then be activated to produce a time-varying magnetic field in the primary coil 106. The time-varying magnetic field induces electric current flow in the secondary coil 100 that is in axial alignment with the primary coil 106. The current can be subsequently distributed to controller 102 and any attached ventricular assist devices 104 or charge storage devices.

To monitor and/or control operating parameters associated with ventricular assist device 104 or any other implanted component, a RF communication link between external communicator 112 and internal controller 102 can be established. RF telemetry circuitry within the controller 102 communicates using RF antenna 110. External RF communicator 112 can be any communication device adapted to transmit and receive RF signals to and from controller 102. The external communicator 112 can, for example, be part of the power source 108. Alternatively, the communicator 112 can be a separate unit. RF antenna 110 can be any form of RF antenna suitable for implantation inside the body. In some cases, RF antenna 110 can be a monopole antenna connected to controller 102.

The configuration shown in FIG. 1 can have several disadvantages, however. Controller 102 is often larger than the secondary coil 100 and, as a result, is typically implanted in the abdominal cavity because its size can be better accommodated. This places controller 102 deeper within the body than secondary coil 100. RF antenna 110, which is connected to controller 102, is also typically disposed deeper within the body. The result is a great deal of signal attenuation during transmission and reception due to the number of intervening layers of muscle, fat, and tissue between RF antenna 110 and external communicator 112.

Such a configuration can also be disadvantageous because it requires that surgeons implant RF antenna 110 separately when implanting the TET system in a patient. This additional component requires added time and can result in a more invasive surgery. The additional component can also be another possible site for infection or other medical complication.

Third, such a configuration can be disadvantageous because it requires an additional connection into the controller 102. This makes the overall implantable TET system more complex and introduces an additional point of potential failure in the system. It is always desirable to reduce complexity and possible modes of failure in systems designed to be implanted in the body for long periods of time.

Figure 2:
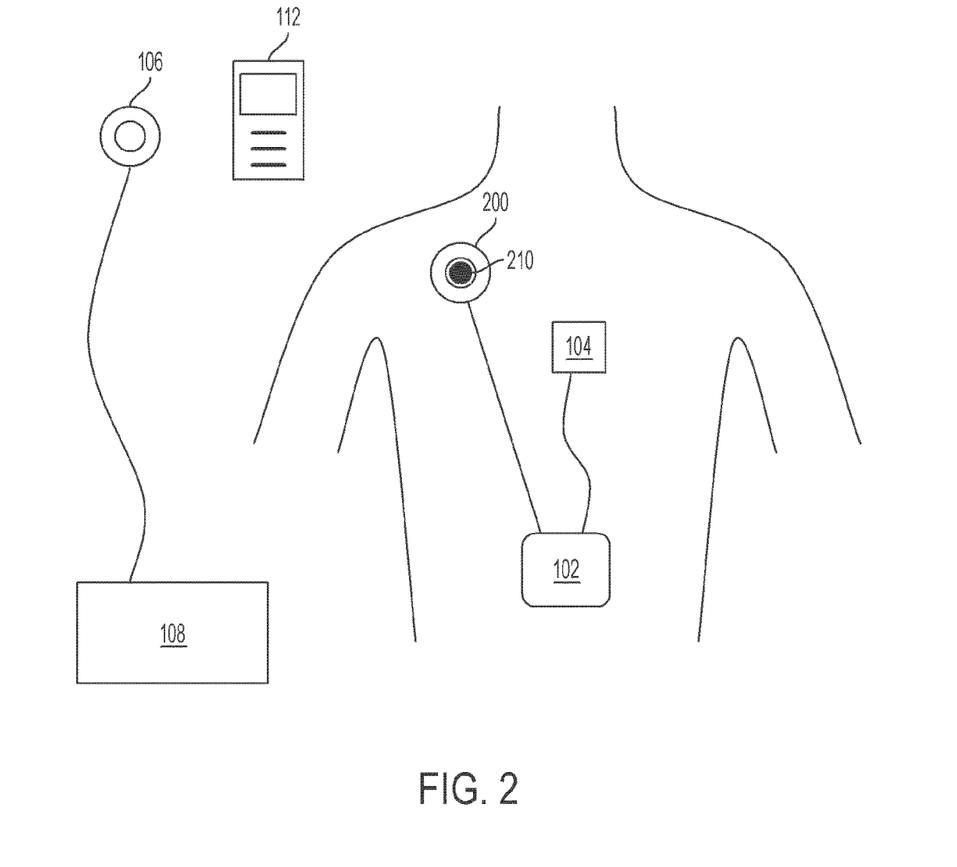
FIG. 2 is an illustration of a TET system according to the present invention.

Accordingly, the present invention is directed to a secondary coil for use in a TET system that has an integrated RF antenna. A TET system according to the teachings of the present invention is illustrated in FIG. 2. The system is generally similar to the one shown in FIG. 1, with the notable difference that the secondary coil 200 is integrated with RF antenna 210.

There are a number of benefits to integrating the secondary coil 200 and radio frequency (RF) antenna 210. For example, integrating the RF antenna 210 into the secondary coil moves the antenna from deep within the body to just below the surface of the skin. This location results in significantly less signal attenuation when communicating with external communicator 112. This means less power can be used to communicate and greater range can be achieved.

Furthermore, integrating the RF antenna into secondary coil 200 reduces the overall number of components and connections that are necessary to implant the TET system in a patient. This, in turn, reduces the invasiveness of the surgery required to implant the system, while also reducing possible sites for infection and modes of failure for the system.

Figure 3:
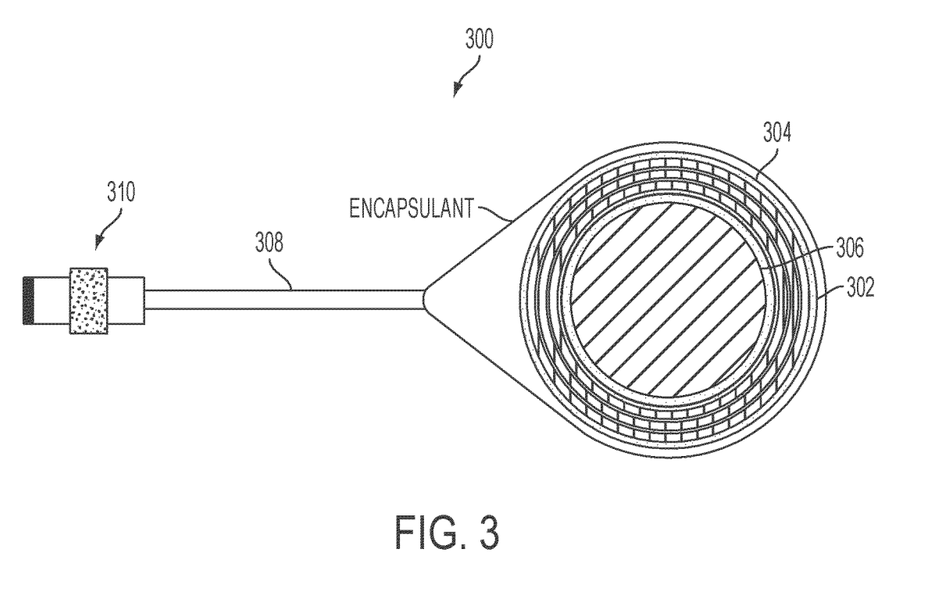
FIG. 3 is an illustration of an exemplary TET secondary coil of the present invention.

FIG. 3 illustrates an exemplary secondary coil 300 of the present invention adapted for disposition within a patient. Secondary coil 300 features a coil winding portion 302 consisting of several turns of conductive wire, a core 304 containing electrical circuitry in connection with coil portion 302, radio frequency (RF) antenna 306, a connecting portion 308, and an interface portion 310.

Coil portion 302 can vary in size and turns of wire depending on numerous factors such as the intended implantation site, the desired driving frequency, etc. In an exemplary embodiment, coil portion 302 comprises 13 turns of Litz wire in a two-inch diameter coil. In addition to the wire, the secondary coil 300 can contain a ferrite core 304 that houses electronic circuitry which rectifies the AC current in the coil portion 302 to provide a regulated DC output voltage to the controller 102 or ventricular assist device 104. Coil portion 302 is typically wound around core 304. An exemplary secondary coil using a ferrite core is described in U.S. Patent Pub. No. 2003/0171792, which is hereby incorporated by reference in its entirety.

In other exemplary embodiments, the ferrite core 304 can be omitted from the secondary coil 300. In such a configuration, the integrated TET power delivery coil and RF antenna would still function as described. Securing the RF antenna in place relative to the coil portion 302 in these embodiments can be accomplished by an encapsulation material, adhesive plastic sheet, or any other method known in the prior art.

The secondary coil also comprises connecting portion 308. In an exemplary embodiment, connecting portion 308 comprises a cable jacket that can carry connecting wires for power delivery and a coaxial cable for communications through RF antenna 306. The length of connecting portion 308 can vary based on, for example, the distance from the implantation site of a secondary coil 300 to a controller 102.

Connecting portion 308 can be coupled to interface portion 310. Interface portion 310 can be used to connect the secondary coil 300 to a controller 102. The interface portion 310 can include any electrical connector known in the art to facilitate modular connection to a controller 102, or can consist of terminal ends of the wires carried by connecting portion 308 that are capable of being electrically connected to a controller. In an exemplary embodiment, interface portion 310 comprises a single modular connector carrying leads for the electrical connection of both the coil and RF antenna 306.

Figure 4A:
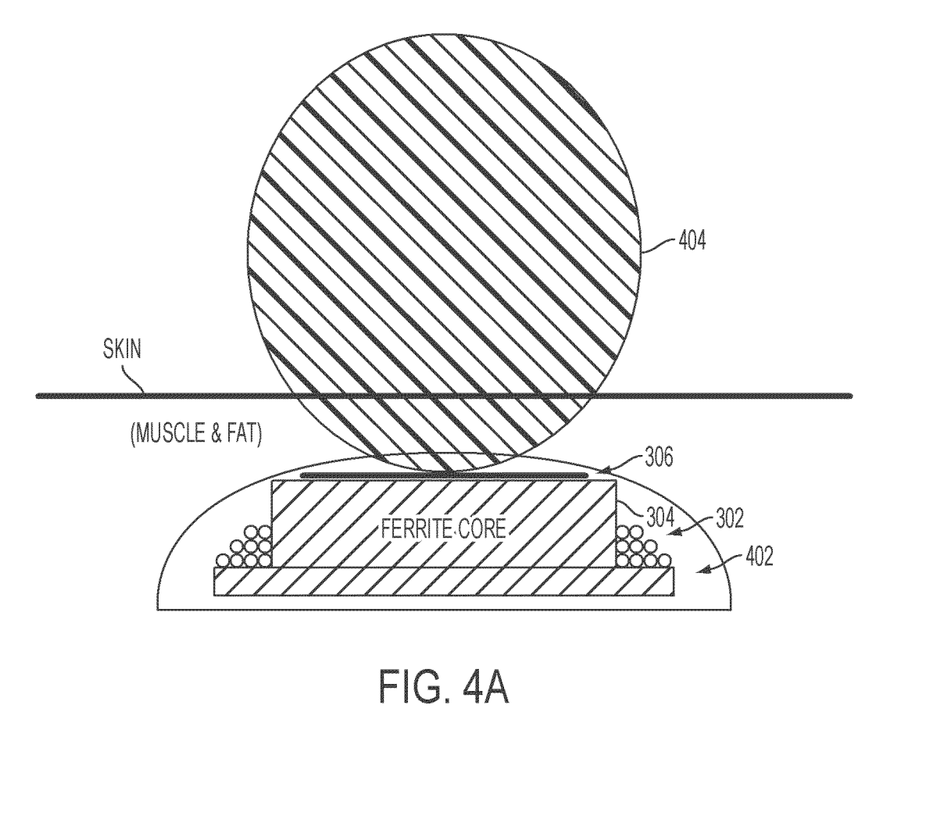
FIG. 4A is a cross-sectional view of the exemplary TET secondary coil shown in FIG. 3.
Figure 4B:
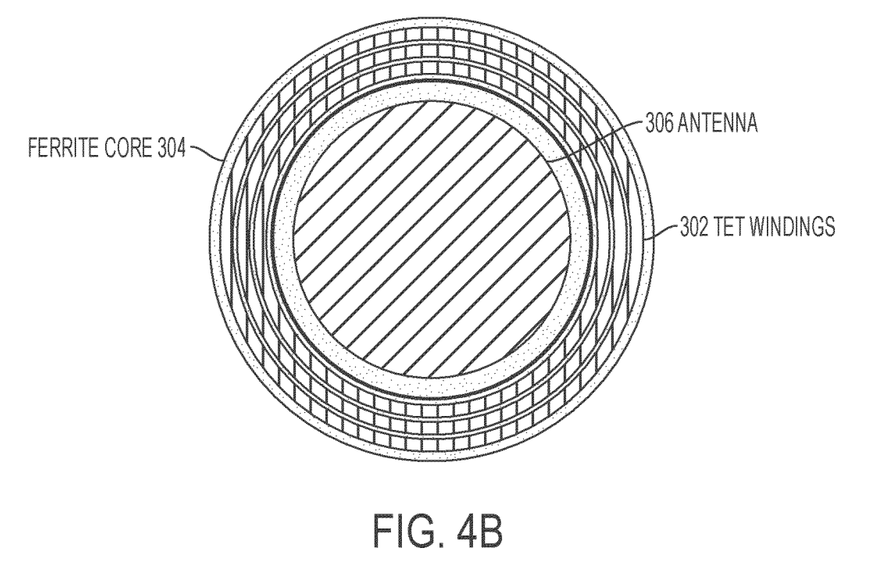
FIG. 4B is a top view of the exemplary TET secondary coil shown in FIG. 3.

RF antenna 306 can be integrated into the secondary coil 300 in a number of ways. In the exemplary embodiment shown in FIG. 3, RF antenna 306 comprises a micro-strip patch antenna that can be laminated to the ferrite core 304. FIGS. 4A and 4B show the ferrite core 304, coil portion 302, and RF antenna 306 in alternative views. After attachment of the RF antenna to the core 304, the secondary coil can be encapsulated in a biocompatible material before implantation. In an exemplary embodiment, the secondary coil 300 can be encapsulated in epoxy 402 and subsequently dipped in ANGIOFLEX®, or a silicone rubber having low permeability and moisture ingress. These materials can prevent moisture ingress into the secondary coil.

Micro-strip patch antennas typically comprise a metal patch separated from a larger ground plane by an air gap or dielectric material. The size of the patch and spacing from the ground plane can be used to tune the operating frequencies of the antenna. Micro-strip patch antennas can be formed in a variety of shapes and sizes, and are relatively inexpensive to manufacture.

One beneficial feature of micro-strip patch antennas is that they have highly directional radiation patterns. Radiation emanates from the metal patch traveling primarily in a direction away from the ground plane. As a result, the strongest gain is found directly above the antenna opposite of the ground plane.

By integrating a micro-strip patch antenna into the secondary coil as shown in FIGS. 3, 4A, and 4B, this characteristic of the antenna can be utilized. An exemplary representative radiation pattern 404 for RF antenna 306 is illustrated in FIG. 4A. The pattern illustrates that the micro-strip patch antenna radiates primarily away from the patient's body through the least amount of skin, muscle, and fat. Correspondingly, a lower transmitter power level can be used since the amount of signal attenuation is minimized. This, in turn, minimizes any potential radiation-induced tissue damage.

Furthermore, technicians or patients operating external communicator 112 have no doubt as to where the device should be positioned in order to receive the best RF signal. This can be particularly helpful in situations where users are attempting to troubleshoot RF communication and want to be sure that signal strength is as high as possible.

Moreover, the dielectric ferrite core 304 mounted underneath the micro-strip patch antenna can serve, in conjunction with the antenna's ground plane, to further direct the radiation of the antenna and limit radiation directed deeper into a patient's body. The end result is a highly directional RF antenna that is configured to transmit through the least amount of tissue possible without wasting energy by also radiating back into a patient's body.

In order to take advantage of the benefits associated with the directionality of micro-strip patch antennas, the secondary coil should be implanted in an orientation that directs the antenna toward the skin surface. An exemplary orientation is shown in the cross-sectional view of FIG. 4A. In order to assist in correctly orienting the secondary coil during implantation, one or more identifying marks or labels can be included on the secondary coil to identify the location of the RF antenna or the proper orientation of the secondary coil.

While a micro-strip patch antenna is one embodiment of an integrated RF antenna, other methods of integration are possible as well. In another exemplary embodiment, the RF antenna comprises a loop antenna that can be wound around the ferrite core 304 outside of the coil portion 302.

In yet another exemplary embodiment, the windings of coil portion 302 can be used as both the TET power receiving coil and the RF antenna. Such an arrangement requires the use of a diplexer to drive the coil portion 302 at the desired RF frequency and the desired TET power delivery frequency. This configuration provides the extra benefit of eliminating the RF antenna as a separate component and using the coil portion 302 for both power delivery and RF communications. This, in turn, reduces the complexity and improves the reliability of the implantable system.

Interference can be a concern when operating the TET power transfer and RF communications systems simultaneously in close proximity. Indeed, concerns over radio interference often result in the separate antennas known in the prior art and shown in FIG. 1. However, interference can be avoided by selecting the operating frequencies of the TET power delivery and RF communications systems such that there is significant separation between the two. Operating frequencies can also be selected so as to avoid the presence of any shared harmonic frequencies.

It is possible to choose operating frequencies that are not significantly separated because signal filtering can be used to prevent interference. The closer the frequencies become, however, the greater amount of filtering is necessary. As a result, operating frequencies with significant separation are preferable because the amount of filtering, and thus the overall complexity of the system, can be minimized.

In an exemplary embodiment, the TET power delivery system can be operated at a frequency below about 30 MHz and the RF communications system can be operated at any frequency suitable for RF communications. Operating the TET power delivery system below about 30 MHz can aid in minimizing tissue-related signal attenuation. In some exemplary embodiments, the TET power delivery system can be operated at a fixed frequency of about 300 KHz and the RF communications system can be operated at a frequency of about 900 MHz. More particularly, in another exemplary embodiment, the TET power delivery system can be operated at 327 KHz and the RF communications system can be operated in a frequency range between about 902 MHz and about 928 MHz. In other exemplary embodiments, the RF communications system can be operated in a frequency range between about 863 MHz and 870 MHz.

Figure 5:
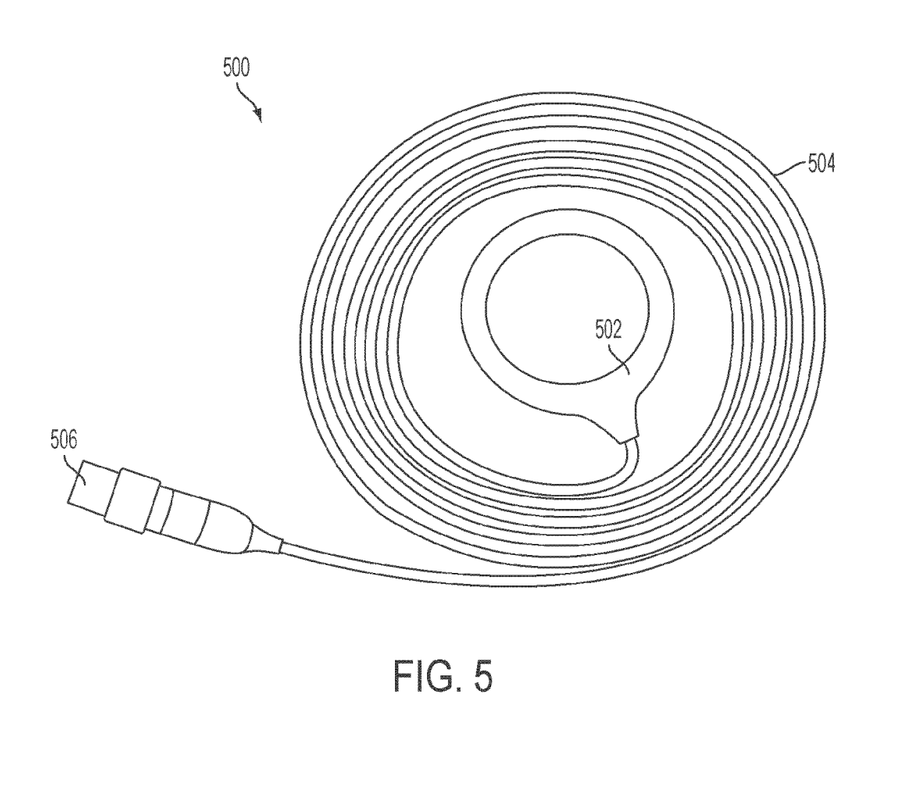
FIG. 5 is an illustration of an exemplary TET primary coil of the present invention.

A secondary coil like the one depicted in FIG. 3 can be inductively coupled with, for example, the primary coil 500 illustrated in FIG. 5. Similar to secondary coil 300, primary coil 500 includes a coil portion 502, a connecting portion 504, and an interface portion 506. In exemplary embodiments, however, primary coil 500 does not contain a ferrite core or RF antenna. Primary coil 500 can be adapted to connect, using interface portion 506, to power supply 108. Power supply 108 can include an external battery pack, wall-powered AC adapter, or other power source, as well as conditioning circuitry that produces a desired voltage, frequency, and current profile.

While the exemplary primary coil 500 illustrated in FIG. 5 does not contain a ferrite core or RF antenna, embodiments that contain these features are not outside the scope of the present invention. By way of non-limiting example, a primary coil having an integrated RF antenna similar to secondary coil 300 could be connected to a combination power supply and external communicator device to both power and bi-directionally communicate with an implanted coil.

In still other embodiments, a primary coil having an integrated RF antenna could be used in connection with a separate power supply and external communicator device by using, for example, separate connecting leads in the connecting portion 504.

In any such embodiments, the placement of an external RF antenna in the primary coil ensures that the antenna can be in close proximity to the implanted RF antenna. More than simple proximity, however, the antenna can be located directly on top of the implanted antenna in the area of strongest gain shown in FIG. 4A. This, again, allows for more reliable communication using less power than conventional RF communication configurations.

Figure 6:
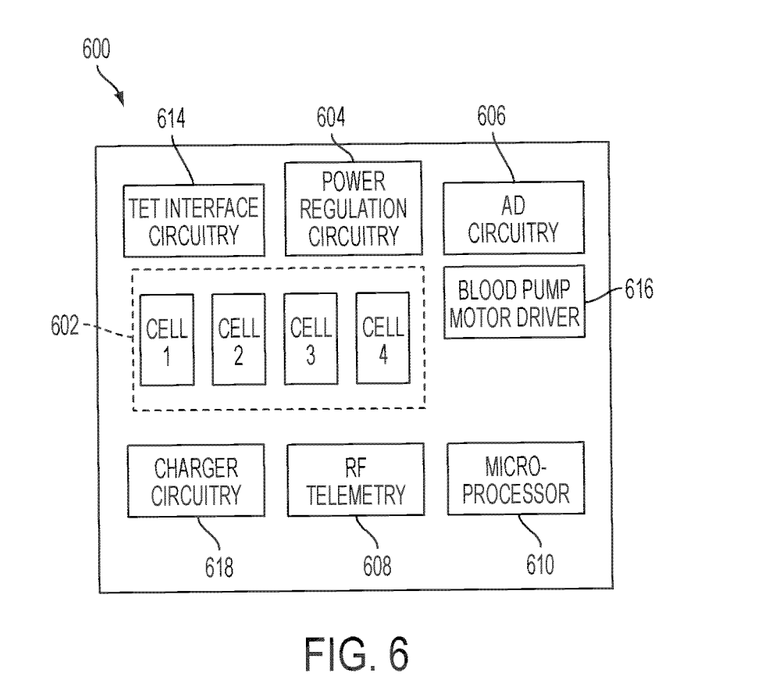
FIG. 6 is a block diagram of an exemplary TET controller of the present invention.

Inside the body, secondary coil 300 can be connected, using interface portion 310, to an implantable device controller. A block diagram of an exemplary controller of the present invention is illustrated in FIG. 6. Controller 600 features a rechargeable battery pack represented by battery cells 602, as well as charger circuitry 618. The controller 600 also contains TET interface circuitry 614 that receives the rectified DC output voltage from secondary coil 300. Power regulation circuitry 604 can also be included to condition the received voltage for use with the rechargeable battery pack, ventricular assist device 104, and other controller components.

Controller 600 also contains A/D circuitry 606 and blood pump motor driver 616 to drive and sense operating parameters of the ventricular assist device 104. Microprocessor 610 coordinates the operation of all of these components to run the controller 600 according to programmed instructions.

Microprocessor uses RF telemetry circuitry 608, in conjunction with integrated RF antenna 306, to communicate with external communicator 112. In such a configuration, external communicator 112 can be used to poll controller 600 for data regarding the operation of the TET system, including the presence of any alarm conditions or other failures. The Controller 600 can independently initiate communication with the external communicator 112 in the event of an internal alarm. Controller 600 can provide data related to any system component either continuously or upon interrogation from external communicator 112. Exemplary parameters include secondary coil input voltage, pump operating speed, battery charge level, etc. External communicator 112 can also be used to send new program instructions to controller 600 to reconfigure its operation. In addition, the external communicator can be used to upload new algorithms or other operational parameters.

The exemplary embodiments shown and described above can also be incorporated into implantable systems that utilize more than one secondary coil. Implanting a plurality of secondary coils can have significant benefits including, for example, allowing a patient to periodically connect a primary coil to a different area of their body, thereby reducing discomfort, as well as allowing a patient to rest in a greater variety of positions. Furthermore, a patient also has the option of connecting more than one primary coil at a time in order to more quickly recharge an implanted battery or other charge storage device.

In exemplary multi-coil embodiments, a plurality of secondary coils like coil 300 shown in FIG. 3 can be implanted in a patient and connected to controller 102. Each secondary coil 300 can have its own RF antenna 306 that can also be connected to controller 102. Using a microprocessor and RF telemetry chip like those shown in FIG. 6, controller 102 can be configured to continually scan among the plurality of secondary coils for the RF antenna receiving the strongest signal quality from, for example, external communicator 112. The controller 102 can then isolate the antenna with the best signal quality for a communication exchange. In some embodiments, the controller can be further configured to continue scanning among the plurality of secondary coils to determine whether any other RF antenna exhibits stronger RF signal quality. The controller can be configured to switch over to the other RF antenna for communication exchange if a stronger signal is detected.

Systems employing a plurality of secondary coils where each coil includes an integrated RF antenna provide several advantages. For example, the implantable system is able to provide the best RF signal path by not only using antennas disposed close to a patient's skin, but also by choosing among two or more antennas to communicate using the antenna receiving the highest signal quality. Furthermore, having two or more RF antennas available for communication provides redundancy in the event that there is a failure of an antenna or secondary coil.

All of the embodiments described above are non-limiting examples of the present invention only. In addition, all papers and publications cited herein are hereby incorporated by reference in their entirety. One of skill in the art will appreciate further features and advantages of the invention based on the above-described embodiments. Accordingly, the invention is not to be limited by what has been particularly shown and described, except as indicated by the appended claims.

What is claimed is:

1. An implantable coil for use in a transcutaneous energy transfer system, comprising:
    a coil winding configured to inductively couple to a primary coil disposed external to a patient's body, the coil winding adapted to produce an electric current in the presence of a time-varying magnetic field operating at a first frequency;
    a ferrite core coupled to the coil winding, said ferrite core having a planar surface substantially parallel to the coil winding;
    circuitry contained in the ferrite core and in electrical communication with the coil winding, the circuitry adapted to receive and condition the electric current produced in the coil winding; and
    a radio frequency (RF) antenna configured to operate at a second frequency different from the first frequency, the RF antenna comprising a micro-strip patch antenna disposed on the planar surface of the ferrite core such that the micro-strip patch antenna is substantially parallel to a skin surface and is disposed between the skin surface and the ferrite core when the coil winding is implanted in the patient at a location just below the skin surface,
    wherein the ferrite core is configured to isolate said circuitry from the first and second frequencies.

2. The implantable coil of claim 1, wherein the coil winding, circuitry, and radio frequency antenna are encapsulated in a biocompatible material.

3. The implantable coil of claim 2, wherein said biocompatible material comprises epoxy.

4. The implantable coil of claim 3, wherein said epoxy is coated with a polyurethane plastic.

5. The implantable coil of claim 3, wherein said epoxy is coated with a silicone rubber.

6. The implantable coil of claim 1, wherein the first frequency is below about 30 MHz.

7. The implantable coil of claim 1, wherein the first frequency is about 300 KHz.

8. The implantable coil of claim 1, wherein the first frequency is 327 KHz.

9. The implantable coil of claim 1, wherein the second frequency is a frequency suitable for RF communication.

10. The implantable coil of claim 1, wherein the second frequency is about 900 MHz.

11. The implantable coil of claim 1, wherein the second frequency is between about 902 MHz and about 928 MHz.

12. The implantable coil of claim 1, wherein the second frequency is between about 863 MHz and about 870 MHz.

13. The implantable coil of claim 1, wherein the micro-strip patch antenna is laminated to the ferrite core.

14. The implantable coil of claim 1, further comprising a connecting portion containing one or more wires connected to the coil winding and the RF antenna.

15. A transcutaneous energy transfer system, comprising:
    a secondary coil adapted for disposition in a patient at a location just below a skin surface, comprising:
        a coil winding adapted to receive transcutaneous energy at a TET operating frequency, the coil winding disposed around a ferrite core having a planar surface substantially parallel to the coil winding; and
        a radio frequency (RF) antenna configured to operate at a RF operating frequency, the RF antenna comprising a micro-strip patch antenna disposed on the planar surface of the ferrite core such that the micro-strip patch antenna is substantially parallel to the skin surface and disposed between the skin surface and the ferrite core when the secondary coil is implanted in the patient;
a primary coil configured to transmit transcutaneous energy to the secondary coil; and
a controller, also adapted for disposition in a patient, comprising circuitry to direct electric current from the secondary coil to charge a storage device and/or power an implantable assist device, wherein the circuitry is disposed within the ferrite core and is isolated from the TET and RF operating frequencies thereby.

16. The system of claim 15, wherein the controller is configured to communicate with an external communicator using the RF antenna in the secondary coil.

17. The system of claim 15, further comprising one or more additional secondary coils.

18. The system of claim 17, wherein the controller is configured to scan among the plurality of secondary coils for a RF antenna having the highest RF signal quality and select the RF antenna having the highest signal quality for use in communicating with an external device.

19. The system of claim 18, wherein the controller is further configured to resume scanning among the plurality of secondary coils after completing communication with the external device.

20. A method of communicating between an external device and an implanted device in a transcutaneous energy transfer (TET) system comprising:
scanning among a plurality of implanted secondary coils each having an integrated radio frequency (RF) antenna to determine which RF antenna has the best RF signal quality, wherein the integrated RF antenna comprises a micro-strip patch antenna disposed on a substantially planar surface of a ferrite core around which coil windings of the secondary coil are disposed such that the micro-strip patch antenna is substantially parallel to a skin surface and is disposed between the skin surface and the ferrite core when the secondary coil is implanted in a patient at a location just below the skin surface;
selecting the RF antenna having the best RF signal quality for a communication exchange between the external device and the implanted device; and
resuming scanning among the plurality of implanted secondary coils to determine whether an other RF antenna exhibits a better RF signal quality.

21. The method of claim 20, wherein the method further comprises switching to the other RF antenna that exhibits better RF signal quality for communication exchange.

* * * * *